United States Patent [19]

Hirsch et al.

[11] Patent Number: 4,766,140

[45] Date of Patent: Aug. 23, 1988

[54] METHOD OF INHIBITING AROMATASE

[75] Inventors: Kenneth S. Hirsch, New Palestine; Charles D. Jones; Harold M. Taylor, both of Indianapolis, all of Ind.

[73] Assignee: Eli Lilly and Company, Indianapolis, Ind.

[21] Appl. No.: 621,417

[22] Filed: Jun. 18, 1984

[51] Int. Cl.[4] ............................................. A61K 31/415
[52] U.S. Cl. ..................... 514/397; 514/396; 514/399
[58] Field of Search ................... 424/273 R; 514/396, 514/397, 399

[56] References Cited

U.S. PATENT DOCUMENTS

| | | | |
|---|---|---|---|
| 3,658,813 | 4/1972 | Godefroi et al. | 260/240 K |
| 3,927,017 | 12/1975 | Heeres et al. | 260/309 |
| 4,036,970 | 7/1977 | Walker et al. | 424/273 |
| 4,062,966 | 12/1977 | Gymer | 424/273 R |
| 4,277,475 | 7/1981 | Vickery | 424/250 |
| 4,301,166 | 11/1981 | Regel et al. | 424/269 |
| 4,358,458 | 11/1982 | Scharwachter et al. | 424/273 R |
| 4,396,771 | 8/1983 | Thorogood | 548/335 |
| 4,405,634 | 9/1983 | Thorogood | 424/273 R |
| 4,413,003 | 11/1983 | Miller et al. | 424/273 R |
| 4,414,210 | 11/1983 | Miller et al. | 424/245 |
| 4,425,354 | 1/1984 | Thorogood | 424/273 R |
| 4,446,145 | 5/1984 | Van Bever | 424/273 R |

OTHER PUBLICATIONS

Carter et al., Chemotherapy of Cancer, 2nd Ed., pp. 361, 364 and 365 (1981).

Derwent 83-736941/33, Abstracting GB No. 2,114,120, 12/17/82.
Derwent 83-730263/32, Abstracting EP No. 84,834, 8/3/83.
Derwent 83-729723/32, Abstracting DE No. 3,202,604, 8/4/83.
Derwent 83-729726/32, Abstracting DE No. 3,202,613, 8/4/83.
Derwent 83-729722/32, Abstracting DE No. 3,202,602, 8/4/83.
Derwent 83-754399/36, Abstracting EP No. 87,148, 8/31/83.
Derwent 83-802291/44, Abstracting DE No. 3,216,301, 10/27/83.
Derwent 78074E/37, Abstracting J5 7128-604, 8/10/82.
Derwent 83-790152/42, Abstracting EP No. 90,993, 10/12/83.
Derwent 97713E/46, Abstracting EP No. 64,244, 11/10/82.
Derwent 97714E/46, Abstracting EP No. 64,245, 11/10/82.
D'Arcy et al., "Progress in Drug Research," vol. 22 (1978) pp. 93–147.

*Primary Examiner*—Allen J. Robinson
*Attorney, Agent, or Firm*—Robert A. Conrad; Leroy Whitaker

[57] ABSTRACT

This invention provides a method of inhibiting aromatase and treating or preventing estrogen-dependent diseases in mammals which comprises administering certain imidazole derivatives.

19 Claims, No Drawings

METHOD OF INHIBITING AROMATASE

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research*, Vol. 42, Suppl. 8:3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer*, 25, 270 (1971)). Two of the known aromatase inhibitors, testolactone and aminoglutethimide, have shown a beneficial effect in treatment of breast cancer. See *Cancer Research*, supra.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer*, 49, 2534 (1982). Aromatase inhibitors have not been tried in this disease, but antiestrogens seem to be of benefit. See *Obstet. Gynecol.*, 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.*, 12, 177 (1980).

It is the purpose of this invention to provide a method for inhibiting the enzyme aromatase in mammals employing certain imidazole derivatives. The invention thus provides for the treatment or prevention of breast cancer and other estrogen-dependent diseases.

SUMMARY OF THE INVENTION

This invention provides for a method of inhibiting aromatase in mammals which comprises administering an aromatase inhibiting amount of an imidazole of the formula

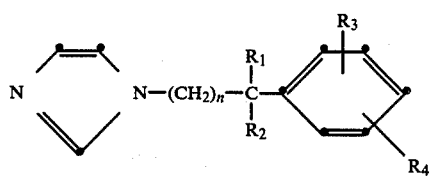

wherein
n is 1 or 2;
$R_1$ is hydrogen, hydroxy, or $-OCH_2R_5$;
$R_2$ is hydrogen or

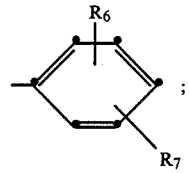

$R_5$ is $-CH=CH_2$, thienyl, halothienyl, or

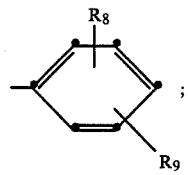

and
$R_3$, $R_4$, $R_6$, $R_7$, $R_8$, and $R_9$ are independently hydrogen, methoxy, halo, trifluoromethyl, or nitro, or a pharmaceutically acceptable salt thereof.

By virtue of their ability to inhibit the enzyme aromatase, the imidazoles of the above formula are useful in the treatment and prevention of estrogen-dependent diseases, especially breast cancer, in mammals.

DETAILED DESCRIPTION AND PREFERRED EMBODIMENT

The term "halo" refers to fluoro, chloro, bromo, and iodo. The term "thienyl" refers to a thiophene group attached through its 2- or 3-position. The term "halothienyl" refers to a thienyl group which has a halo group attached to one of the remaining carbon atoms.

A preferred group of compounds useful in the method of this invention are those wherein:
(a) $R_2$ is hydrogen, and
(b) at least one of $R_3$ and $R_4$ is halo, preferably chloro, especially in the para position of the phenyl ring.

The compounds used in this invention are known in the art or are prepared by published methods well known to those skilled in the art. Such publications include, but are not limited to, U.S. Pat. Nos. 4,062,966 and 4,396,771. Both patents are expressly incorporated in this application by reference. The compounds as disclosed in the patents are described as being useful as fungicides and in the treatment of thromboembolic disorders, shock, and angina pectoris. The patents do not disclose any utility related to the inhibition of aromatase or the treatment of estrogen-dependent diseases.

As will be recognized by those skilled in the art, the compounds of the above formula can contain an asymmetric carbon atom. This invention is not limited to any particular isomer but includes the individual enantiomers as well as the racemates of the compounds.

The pharmaceutically acceptable acid addition salts used in this invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, $\beta$-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

The compounds used in this invention are useful in preventing or therapeutically treating estrogen-dependent diseases, including breast cancer, in mammals by virtue of their ability to inhibit the enzyme aromatase. The ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 $\mu$M 4-androstene-3,17-dione, 100,000 dpm 1,2[$^3$H]-androstenedione, the microsomes and a NADPH generating system. The concentrations of the inhibitors tested ranged between 0.005 and 10 $\mu$M. In this assay, aromatization of androstenedione results in the production of [$^3$H]-H$_2$O which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in $\mu$M required to produce a 50% inhibition of enzyme activity (EC$_{50}$) when the concentration of substrate (androstenedione) is 0.1 $\mu$M. The EC$_{50}$'s of certain of the compounds of the above formula are summarized in Table 1.

TABLE 1

| Aromatose Inhibition in the Rat Ovarian Microsome Assay | |
|---|---|
| Compound | EC$_{50}$* |
| 1-($\beta$-phenylethyl)imidazole | 0.63 |
| 1-(3-phenylpropyl)imidazole | 0.49 |
| 1,1-diphenyl-3-(1-imidazolyl)-1-propanol | 0.084 |
| 1-[2,4-dichloro-$\beta$-(2,4-dichlorobenzyloxy)phenylethyl]imidazole | 0.31 |
| 1-[2-(2,4-dichlorophenyl)-2-(2-propenyloxy)ethyl]-1H-imidazole | 0.042 |
| 1-[2-(4-nitrophenyl)ethyl]-1H-imidazole | <0.05 |
| 1-(3,4-dichlorophenylethyl)-1H-imidazole, oxalic acid salt | 0.084 |
| 1-(2-[(2-chloro-3-thienyl)-methoxy]-2-[2,4-dichlorophenyl]ethyl)-1H-imidazole | 0.060 |
| $\alpha$-(2,5-dimethoxyphenyl)-1H-imidazole-1-ethanol nitrate | 1.5 |

*Concentration of compound in $\mu$M required to achieve 50% inhibition of aromatase activity when substrate concentration is 0.1 $\mu$M.

By virtue of their ability to inhibit the enzyme aromatase, the compounds employed in the method of this invention are able to inhibit the synthesis of estrogens in mammals, thereby making the compounds useful in the treatment of estrogen-dependent diseases, such as breast cancer. This in vivo activity was demonstrated in the following test system.

DMBA-Induced Mammary Tumor Inhibition

Mammary tumors were produced in female Sprague-Dawley rats which were 50-60 days old by the gavage administration of 20 mg of 7,12-dimethylbenz[a]anthracene (DMBA). About six weeks after DMBA administration, the mammary glands were palpated at weekly intervals for the appearance of tumors. Whenever one or more tumors appeared and were measurable in an animal, that animal was selected for experimentation. An attempt was made to uniformly distribute the various sizes of tumors in the treated and control groups such that one group did not start with rats having tumors which, on the average, were significantly larger than those of any other group. Each control and test group contained 8 animals. The test compound was dissolved in corn oil and administered subcutaneously once daily. Every experiment included a group of control rats having tumors and were given corn oil vehicle subcutaneously. The tumors were measured at the start of the experiments and generally had an area of approximately 15-100 mm$_2$. The area of each tumor was calculated by multiplying the shortest and longest diameters of the tumor. The treatment and measurement of animals continued for 3 weeks at which time the final areas of the tumors were determined. The change in the mean tumor area was determined, and the mean change was analyzed for its significance using Dunnett's t-test. The results of this test are shown in Table 2 below.

TABLE 2

| | | | | Mean Tumor Area (mm$^2$) | |
|---|---|---|---|---|---|
| Test No. | Compound | Dose* | Duration of Test | Start | Finish |
| I | Control | — | 3 weeks | 72.2 | 392.0 |
| | 1-[2-(2,4-dichlorophenyl)-2-(2-propenyloxy)ethyl]-1H—imidazole | 4 mg/kg | | 55.2 | 119.0+ |

*Daily dose given subcutaneously.
+statistically different from control, p < 0.05.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one active compound of the above formula.

Such pharmaceutical compositions comprise as active ingredient a compound of the above formula associated with a pharmaceutically acceptable carrier. In making the compositions, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

We claim:

1. A method of inhibiting aromatase in a mammal which comprises administering to said mammal an aromatase inhibiting amount of a compound of the formula

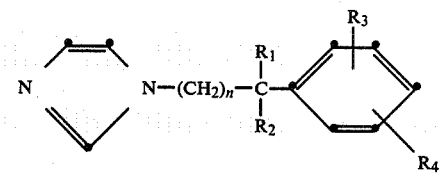

wherein
n is 1 or 2;
$R_1$ is hydrogen, hydroxy, or $-OCH_2R_5$;
$R_2$ is hydrogen or

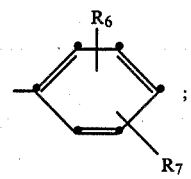

$R_5$ is $-CH=CH_2$, thienyl, halothienyl, or

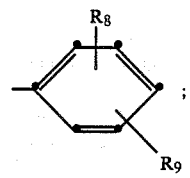

and
$R_3$, $R_4$, $R_6$, $R_7$, $R_8$, and $R_9$ are independently hydrogen, methoxy, halo, trifluoromethyl, or nitro, or a pharmaceutically acceptable salt thereof.

2. The method according to claim 1 employing a compound wherein $R_2$ is hydrogen.

3. The method according to claim 2 employing a compound wherein one of $R_3$ and $R_4$ is chloro.

4. The method according to claim 3 employing a compound wherein one of $R_3$ and $R_4$ is chloro in the para-position.

5. The method according to claim 4 employing 1-[2,4-dichloro-β-(2,4-dichlorobenzyloxy)phenethyl]imidazole or a pharmaceutically acceptable salt thereof.

6. The method according to claim 4 employing 1-[2-(2,4-dichlorophenyl)-2-(2-propenyloxy)ethyl]-1H-imidazole or a pharmaceutically acceptable salt thereof.

7. The method according to claim 4 employing 1-(2-[(2-chloro-3-thienyl)methoxy]-2-[2,4-dichlorophenyl]ethyl)-1H-imidazole or a pharmaceutically acceptable salt thereof.

8. A method of treating estrogen-dependent diseases in a mammal which comprises administering an effective amount of a compound according to the formula

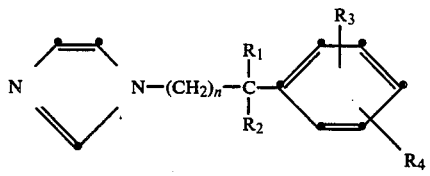

wherein n is 1 or 2;

R₁ is hydrogen, hydroxy, or —OCH₂R₅;

R₂ is hydrogen or

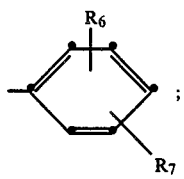

R₅ is —CH=CH₂, thienyl, halothienyl, or

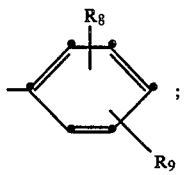

and

R₃, R₄, R₆, R₇, R₈, and R₉ are independently hydrogen, methoxy, halo, trifluoromethyl, or nitro, or a pharmaceutically acceptable salt thereof.

9. The method according to claim 8 employing a compound wherein R₂ is hydrogen.

10. The method according to claim 9 employing a compound wherein one of R₃ and R₄ is chloro in the para-position.

11. The method according to claim 10 employing 1-[2,4-dichloro-β-(2,4-dichlorobenzyloxy)phenethyl]imidazole or a pharmaceutically acceptable salt thereof.

12. The method according to claim 10 employing 1-[2-(2,4-dichlorophenyl)-2-(2-propenyloxy)ethyl]-1H-imidazole or a pharmaceutically acceptable salt thereof.

13. The method according to claim 10 employing 1-(2-[(2-chloro-3-thienyl)methoxy]-2-[2,4-dichlorophenyl]ethyl)-1H-imidazole or a pharmaceutically acceptable salt thereof.

14. The method according to claim 8 wherein the estrogen-dependent disease is breast carcinoma cancer.

15. The method according to claim 14 emplcying a compound wherein R₂ is hydrogen.

16. The method according to claim 15 employing a compound wherein one of R₃ and R₄ is chloro in the para-position.

17. The method according to claim 16 employing 1-(2-[(2-chloro-3-thienyl)methoxy]-2-[2,4-dichlorophenyl]ethyl)-1H-imidazole or a pharmaceutically acceptable salt thereof.

18. The method according to claim 16 employing 1-[2,4-dichloro-β-(2,4-dichlorobenzyloxy)phenethyl]imidazole or a pharmaceutically acceptable salt thereof.

19. The method according to claim 16 employing 1-[2-(2,4-dichlorophenyl)-2-(2-propenyloxy)ethyl]-1H-imidazole or a pharmaceutically acceptable salt thereof.

* * * * *